US009597056B2

(12) United States Patent
Summers et al.

(10) Patent No.: US 9,597,056 B2
(45) Date of Patent: Mar. 21, 2017

(54) METHOD AND SYSTEMS FOR WEIGHT ADJUSTMENT OF AN AUTOMATED BREAST ULTRASOUND SYSTEM

(71) Applicant: General Electric Company, Schenectady, NY (US)

(72) Inventors: Douglas G. Summers, Palo Alto, CA (US); Jiayu Chen, Palo Alto, CA (US)

(73) Assignee: General Electric Company, Schenectady, NY (US)

( * ) Notice: Subject to any disclaimer, the term of this patent is extended or adjusted under 35 U.S.C. 154(b) by 499 days.

(21) Appl. No.: 14/042,565

(22) Filed: Sep. 30, 2013

(65) Prior Publication Data

US 2015/0094588 A1    Apr. 2, 2015

(51) Int. Cl.
*A61B 8/00* (2006.01)
*A61B 8/08* (2006.01)

(52) U.S. Cl.
CPC .......... *A61B 8/4218* (2013.01); *A61B 8/0825* (2013.01); *A61B 8/403* (2013.01); *A61B 8/44* (2013.01)

(58) Field of Classification Search
CPC combination set(s) only.
See application file for complete search history.

(56) References Cited

U.S. PATENT DOCUMENTS

| | | | |
|---|---|---|---|
| 5,820,549 A | 10/1998 | Marian, Jr. | |
| 8,162,833 B2 | 4/2012 | Zhang et al. | |
| 8,184,882 B2 | 5/2012 | Yu et al. | |
| 8,317,702 B2 | 11/2012 | Yu et al. | |
| 2002/0064048 A1* | 5/2002 | Sander | F16M 11/08 362/401 |
| 2006/0241423 A1 | 10/2006 | Anderson et al. | |
| 2008/0142313 A1* | 6/2008 | Yumura | B66B 5/16 187/394 |
| 2008/0269613 A1 | 10/2008 | Summers et al. | |
| 2010/0152589 A1* | 6/2010 | Asai | A61B 8/42 600/459 |
| 2010/0163694 A1* | 7/2010 | Fadler | A61B 8/0825 248/125.2 |
| 2010/0204578 A1* | 8/2010 | Schmidt | A61B 8/4218 600/443 |
| 2010/0256500 A1 | 10/2010 | Anderson et al. | |
| 2012/0130241 A1 | 5/2012 | Wang et al. | |
| 2012/0302887 A1 | 11/2012 | Anderson et al. | |

* cited by examiner

*Primary Examiner* — Katherine Fernandez
*Assistant Examiner* — Farshad Negarestan
(74) *Attorney, Agent, or Firm* — John D. Russell (57) ABSTRACT

Various methods and systems are provided for imaging a tissue. In one example, a system comprises an adjustable arm, a scanning assembly attached to a first end of the adjustable arm, a counterweight coupled to a second end of the adjustable arm, and a weight adjustment system coupled to the counterweight and configured to modify an effective weight of the scanning assembly.

18 Claims, 6 Drawing Sheets

METHOD AND SYSTEMS FOR WEIGHT ADJUSTMENT OF AN AUTOMATED BREAST ULTRASOUND SYSTEM

FIELD

Embodiments of the subject matter disclosed herein relate to medical imaging and the facilitation of ultrasonic tissue scanning

BACKGROUND

Volumetric ultrasound scanning of the breast may be used as a complementary modality for breast cancer screening. Volumetric ultrasound scanning usually involves the movement of an ultrasound transducer relative to a tissue sample and the processing of resultant ultrasound echoes to form a data volume representing at least one acoustic property of the tissue sample. Whereas a conventional two-dimensional x-ray mammogram only detects a summation of the x-ray opacity of individual slices of breast tissue over the entire breast, ultrasound can separately detect the sonographic properties of individual slices of breast tissue, and therefore may allow detection of breast lesions where x-ray mammography alone fails. Further, volumetric ultrasound offers advantages over x-ray mammography in patients with dense breast tissue (e.g., high content of fibroglandular tissues). Thus, the use of volumetric ultrasound scanning in conjunction with conventional x-ray mammography may increase the early breast cancer detection rate.

In one example, a full-field breast ultrasound (FFBU) scanning apparatus may be used to image breast tissue in one or more planes. One side of an at least partially conformable, substantially taut membrane or film sheet compresses the breast. A transducer translation mechanism maintains an ultrasound transducer in contact with the other side of the film sheet while translating the ultrasound transducer thereacross to scan the breast. Prior to initiating the scanning, a user of the scanning apparatus may place the ultrasound transducer on the patient tissue and apply a downward force on the transducer to compress the tissue in order to properly image the tissue. However, the user may become fatigued and decrease the pressure applied to the scanning apparatus as the scanning progresses, compromising the quality of the acquired images.

BRIEF DESCRIPTION

In one embodiment, a system for imaging a tissue comprises an adjustable arm, a scanning assembly attached to a first end of the adjustable arm, a counterweight coupled to a second end of the adjustable arm, and a weight adjustment system coupled to the counterweight and configured to modify an effective weight of the scanning assembly.

In this way, the counterweight and weight adjustment system may counterbalance the scanning assembly while the scanning assembly is positioned on a tissue to be imaged, allowing the scanning assembly to be neutrally buoyant in space during the positioning. Once the scanning assembly has been positioned on the tissue, the effective weight of the scanning assembly may be increased by the weight adjustment system to apply pressure on the tissue, relieving the user's applied force, yet still compressing the tissue for imaging and still maintaining the moveability of the scanning assembly relative to the patient. By doing so, a more consistent amount of pressure may be automatically provided by the scanning assembly rather than relying on the user to apply pressure during the scanning procedure. Further, the patient is not locked in place by the scanning assembly. Thus, high-quality images may be obtained throughout the entirety of the scanning procedure while improving both patient and user comfort.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

The following description relates to various embodiments of a weight adjustment system for a full-field breast ultrasound (FFBU) scanning apparatus. X-ray mammography is the most commonly used imaging method for mass breast cancer screening. However, x-ray mammograms only detect a summation of the x-ray opacity of individual slices over the entire breast. Alternatively, ultrasound imaging can separately detect sonographic properties of individual slices of breast tissue, thereby enabling users to detect breast lesions where x-ray mammography alone may fail.

Another well-known shortcoming of x-ray mammography practice is found in the case of dense-breasted women, including patients with high content of fibroglandular tissues in their breasts. Because fibroglandular tissues have higher x-ray absorption than the surrounding fatty tissues, portions of breasts with high fibroglandular tissue content are not well penetrated by x-rays and thus the resulting mammograms contain reduced information in areas where fibroglandular tissues reside. Thus, the use of volumetric ultrasound scanning in conjunction with conventional x-ray mammography may increase the early breast cancer detection rate.

Figure 1:
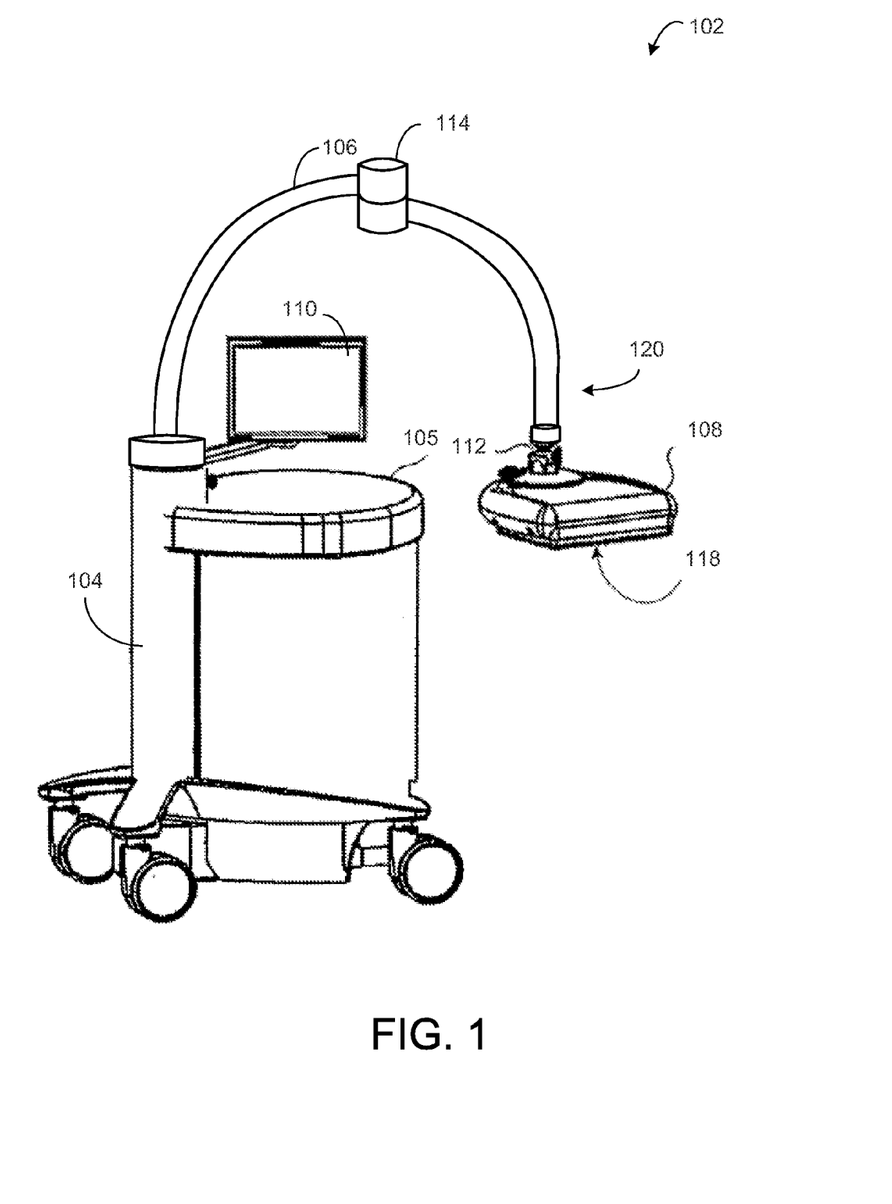
FIG. 1 shows a perspective view of a scanning apparatus according to an embodiment of the invention.
Figure 2:
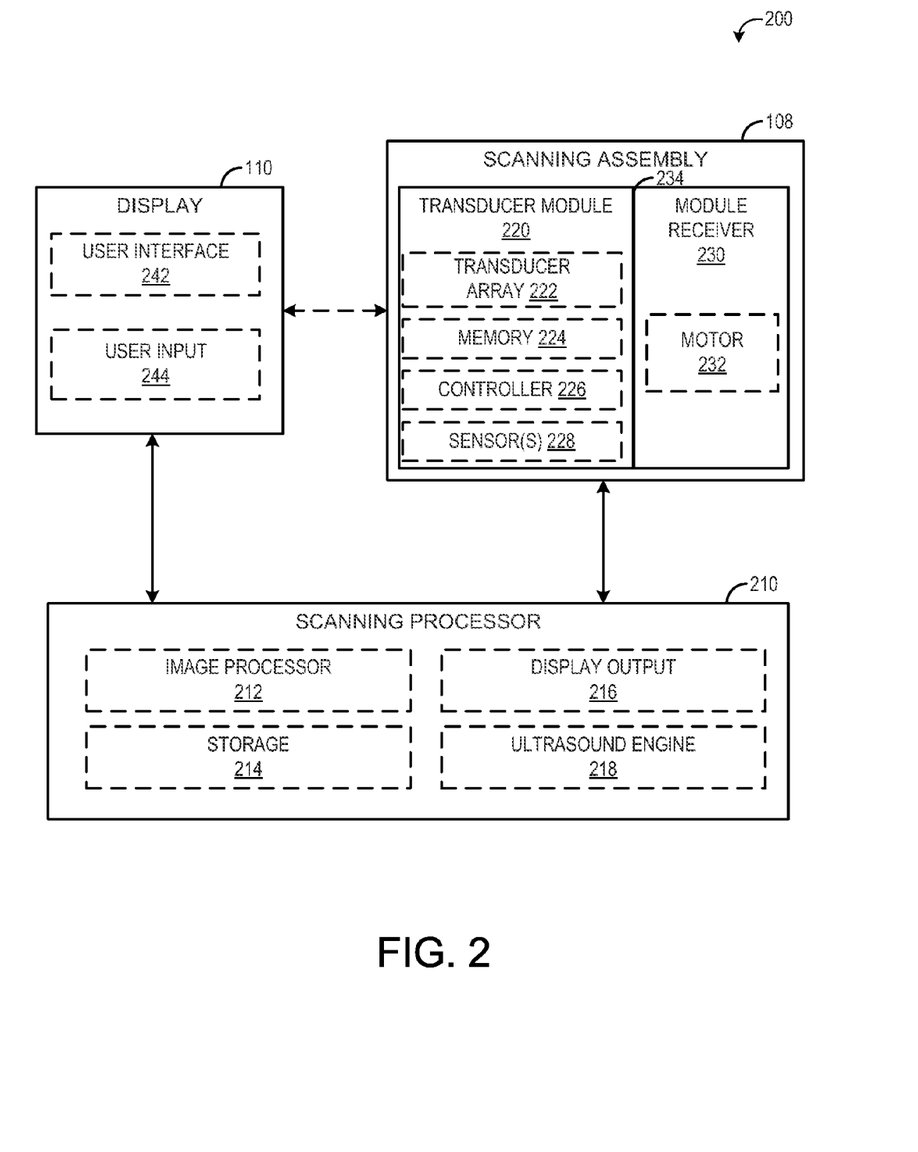
FIG. 2 shows a schematic of various system components of a scanning apparatus according to an embodiment of the invention.

In one example, a full-field breast ultrasound (FFBU) scanning apparatus, such as the FFBU scanning apparatus depicted in FIGS. 1-2, compresses a breast in a generally chestward or head-on direction and ultrasonically scans the breast. In another example, the FFBU scanning apparatus may compress a breast along planes such as the craniocaudal (CC) plane, the mediolateral oblique (MLO) plane, or the like. A compression/scanning assembly of the FFBU scanning apparatus may include an at least partially conformable, substantially taut membrane or film sheet, an ultrasound transducer, and a transducer translation mechanism. One side of the taut membrane or film sheet compresses the breast. The transducer translation mechanism maintains the ultrasound transducer in contact with the other side of the film sheet while translating the ultrasound transducer thereacross to scan the breast.

Typically, to maintain the transducer in contact with the film sheet and breast, a user of the transducer (such as a nurse, technician, or physician) physically applies a downward force on the transducer (e.g., in a direction toward the tissue to be scanned). In order to collect high-quality images, particularly of a dense tissue such as breast tissue, a considerable amount of force may be placed on the transducer to compress the tissue. Over time, the force applied by the user may decrease and/or may be applied unequally, resulting in degraded images.

According to embodiments disclosed herein and described in more detail below with respect to FIGS. 3-5, a scanning assembly (including the transducer) coupled to an adjustable arm may be counterbalanced by a counterweight and weight adjustment system. Once the scanning assembly is positioned on the tissue to be imaged, the effective weight of the scanning assembly may be adjusted by the weight adjustment system. For example, the weight adjustment system may exert an upward force on the counterweight, thus increasing the load placed on the imaged tissue by the scanning assembly. During the adjustment of the effective weight of the scanning assembly and during subsequent scanning, the scanning assembly may remain vertically movable, allowing patient respiration or other motion without disrupting the force applied on the tissue by the scanning assembly.

Although several examples herein are presented in the particular context of human breast ultrasound, it is to be appreciated that the present teachings are broadly applicable for facilitating ultrasonic scanning of any externally accessible human or animal body part (e.g., abdomen, legs, feet, arms, neck, etc.). Moreover, although several examples herein are presented in the particular context of mechanized scanning (i.e., in which the ultrasound transducer is moved by a robot arm or other automated or semi-automated mechanism), it is to be appreciated that one or more aspects of the present teachings can be advantageously applied in a handheld scanning context.

FIG. 1 illustrates a perspective view of a full-field breast ultrasound (FFBU) scanning apparatus 102 according to an embodiment, comprising a frame 104, an ultrasound processor housing 105 that contains an ultrasound processor, a movable and adjustable support arm 106 (e.g., adjustable arm) including a hinge joint 114, a compression/scanning assembly 108 connected to a first end 120 of the adjustable arm 106 via a ball-and-socket connector (e.g., ball joint) 112, and a display 110 connected to the frame 104. The display 110 is coupled to the frame 104 at an interface where the adjustable arm 106 enters into the frame 104. As a result of being directly coupled to the frame 104 and not to the adjustable arm 106, the display 110 does not affect a weight of the adjustable arm 106 and a counterbalance mechanism of the adjustable arm 106. In one example, the display 110 is rotatable in a horizontal and lateral direction (e.g., rotatable around a central axis of the frame 104), but not vertically movable. In an alternate example, the display 110 may also be vertically movable. While FIG. 1 depicts the display 110 coupled to the frame 104, in other examples the display 110 may be coupled to a different component of the scanning apparatus 102, such as coupled to the ultrasound processor housing 105, or located remotely from the scanning apparatus 102.

In one embodiment, the adjustable arm 106 is configured and adapted such that the compression/scanning assembly 108 is either (i) neutrally buoyant in space, or (ii) has a light net downward weight (e.g., 1-2 kg) for breast compression, while allowing for easy user manipulation. In alternate embodiments, the adjustable arm 106 is configured such that the compression/scanning assembly 108 is neutrally buoyant in space during positioning the scanner on the patient's tissue. Then, after positioning the compression/scanning assembly 108, internal components of the scanning apparatus 102 may be adjusted to apply a desired downward weight for breast compression and increased image quality. In one example, the downward weight (e.g., force) may be in a range of 2-11 kg. Additional details regarding adjusting the effective weight of the scanning assembly 108 on a patient will be explained below with respect to FIGS. 3-6.

As introduced above, the adjustable arm 106 includes a hinge joint 114. The hinge joint 114 bisects the adjustable arm 106 into a first arm portion and a second arm portion. The first arm potion is coupled to the compression/scanning assembly 108 and the second arm portion is coupled to the frame 104. The hinge joint 114 allows the second arm portion to rotate relative to the second arm portion and the frame 104. For example, the hinge joint 114 allows the compression/scanning assembly 108 to translate laterally and horizontally, but not vertically, with respect to the second arm portion and the frame 104. In this way, the compression/scanning assembly 108 may rotate toward or away from the frame 104. However, the hinge joint 114 is configured to allow the entire adjustable arm 106 (e.g., the first arm portion and the second arm portion) to move vertically together as one piece (e.g., translate upwards and downwards with the frame 104).

The compression/scanning assembly 108 comprises an at least partially conformable membrane 118 in a substantially taut state for compressing a breast, the membrane 118 having a bottom surface contacting the breast while a transducer is swept across a top surface thereof to scan the breast. In one example, the membrane is a taut fabric sheet. Optionally, the adjustable arm 106 may comprise potentiometers (not shown) to allow position and orientation sensing for the compression/scanning assembly 108, or other types of position and orientation sensing (e.g., gyroscopic, magnetic, optical, radio frequency (RF)) can be used. Within ultrasound processor housing 105 may be provided a fully functional ultrasound engine for driving an ultrasound transducer and generating volumetric breast ultrasound data from the scans in conjunction with the associated position and orientation information. In embodiments, the volumetric scan data may be transferred to another computer system for further processing using any of a variety of data transfer methods known in the art, or the volumetric scan data may be processed by the ultrasound engine. A general purpose computer/processor, which may be integrated with the ultrasound engine, may also be provided for general user interfacing and system control. The general purpose computer may be a self-contained stand-alone unit, or may be remotely controlled, configured, and/or monitored by a remote station connected across a network.

FIG. 2 is a block diagram 200 schematically illustrating various system components of the scanning apparatus 102, including the scanning assembly 108, display 110, and a scanning processor 210. Scanning processor 210 may be included within ultrasound processor housing 105 of the scanning apparatus 102 in one example. As illustrated in the embodiment of FIG. 2, the scanning assembly 108, display 110, and scanning processor 210 are separate components in communication with each other; however, in some embodiments one or more of the components may be integrated (e.g., the display and scanning processor may be included in a single component).

Referring first to the scanning assembly 108, it comprises a transducer module 220 connected to a module receiver 230. The module receiver 230 may be positioned within a housing (attached to the arm 106 of the scanning apparatus, for example) that is configured to remain stationary during scanning, while the module receiver 230 is configured to translate with respect to the housing during scanning. In order to automatically translate with respect to the housing during scanning, the module receiver includes a motor 232 activated by the scanning processor 210, as explained below.

The transducer module 220 comprises a transducer array 222 of transducer elements, such as piezoelectric elements, that convert electrical energy into ultrasound waves and then detect the reflected ultrasound waves. The transducer module 220 is configured to be removably coupled with the module receiver 230 via a connection 234. The connection 234 may include complementary connectors on the transducer module and module receiver (e.g., a first connector on the transducer module that is configured to connect with a second connector on the module receiver) in order to establish both a mechanical connection and an electrical connection between the module receiver and the transducer module.

The transducer module 220 may further include a memory 224. Memory 224 may be a non-transitory memory configured to store various parameters of the transducer module 220, such as transducer usage data (e.g., number of scans performed, total amount of time spent scanning, etc.), as well as specification data of the transducer (e.g., number of transducer array elements, array geometry, etc.) and/or identifying information of the transducer module 220, such as a serial number of the transducer module. Memory 224 may include removable and/or permanent devices, and may include optical memory, semiconductor memory, and/or magnetic memory, among others. Memory 224 may include volatile, nonvolatile, dynamic, static, read/write, read-only, random-access, sequential-access, and/or additional memory. In an example, memory 224 may include RAM. Additionally or alternatively, memory 224 may include EEPROM.

Memory 224 may store non-transitory instructions executable by a controller or processor, such as controller 226, to carry out one or more methods or routines as described herein below. Controller 226 may receive output from various sensors 228 of the transducer module 220 and trigger actuation of one or more actuators and/or communicate with one or more components in response to the sensor output. Sensors 228 may include one or more pressure sensors and/or one or more temperature sensors. During scanning, the pressure across the scanning assembly 108 may be measured by the pressure sensors, and if the pressure distribution across the transducer module is not equal, a user may be notified (via user interface 242 of display 110, for example) to reposition the scanning assembly 108. Further, in some embodiments, to initiate scanning, motor 232 may be activated via a signal from controller 226. However, in other embodiments, motor 232 may be activated via a signal from a separate scanning processor 210, explained below.

Scanning assembly 108 may be in communication with scanning processor 210, to send raw scanning data to an image processor, for example. Additionally, data stored in memory 224 and/or output from sensors 228 may be sent to scanning processor 210 in some examples. Further, various actions of the scanning assembly 108 (e.g., translation of the module receiver 230, activation of the transducer elements, etc.) may be initiated in response to signals from the scanning processor 210. Scanning assembly 108 may optionally communicate with display 110, in order to notify a user to reposition the scanning assembly, as explained above, or to receive information from a user (via user input 244), for example.

Turning now to scanning processor 210, it includes an image processor 212, storage 214, display output 216, and ultrasound engine 218. Ultrasound engine 218 may drive activation of the transducer elements of the transducer array 222 of transducer module 220 and, in some embodiments, may activate motor 232. Further, ultrasound engine 218 may receive raw image data (e.g., ultrasound echoes) from the scanning assembly 108. The raw image data may be sent to image processor 212 and/or to a remote processor (via a network, for example) and processed to form a displayable image of the tissue sample. It is to be understood that the image processor 212 may be included with the ultrasound engine 218 in some embodiments.

Information may be communicated from the ultrasound engine 218 and/or image processor 212 to a user of the scanning apparatus 102 via the display output 216 of the scanning processor 210. In one example, the user of the scanning apparatus may include an ultrasound technician, nurse, or physician such as a radiologist. For example, processed images of the scanned tissue may be sent to the display 110 via the display output 216. In another example, information relating to parameters of the scan, such as the progress of the scan, may be sent to the display 110 via the display output 216. The display 110 may include a user interface 242 configured to display images or other information to a user. Further, user interface 242 may be configured to receive input from a user (such as through user input 244) and send the input to the scanning processor 210. User input 244 may be a touch screen of the display 110 in one example. However, other types of user input mechanisms are possible, such as a mouse, keyboard, etc.

Scanning processor 210 may further include storage 214. Similar to memory 224, storage 214 may include removable and/or permanent devices, and may include optical memory, semiconductor memory, and/or magnetic memory, among others. Storage 214 may include volatile, nonvolatile, dynamic, static, read/write, read-only, random-access, sequential-access, and/or additional memory. Storage 214 may store non-transitory instructions executable by a controller or processor, such as ultrasound engine 218 or image processor 212, to carry out one or more methods or routines as described herein below. Storage 214 may store raw image data received from the scanning assembly 108, processed image data received from image processor 212 or a remote processor, and/or additional information.

Figure 3:
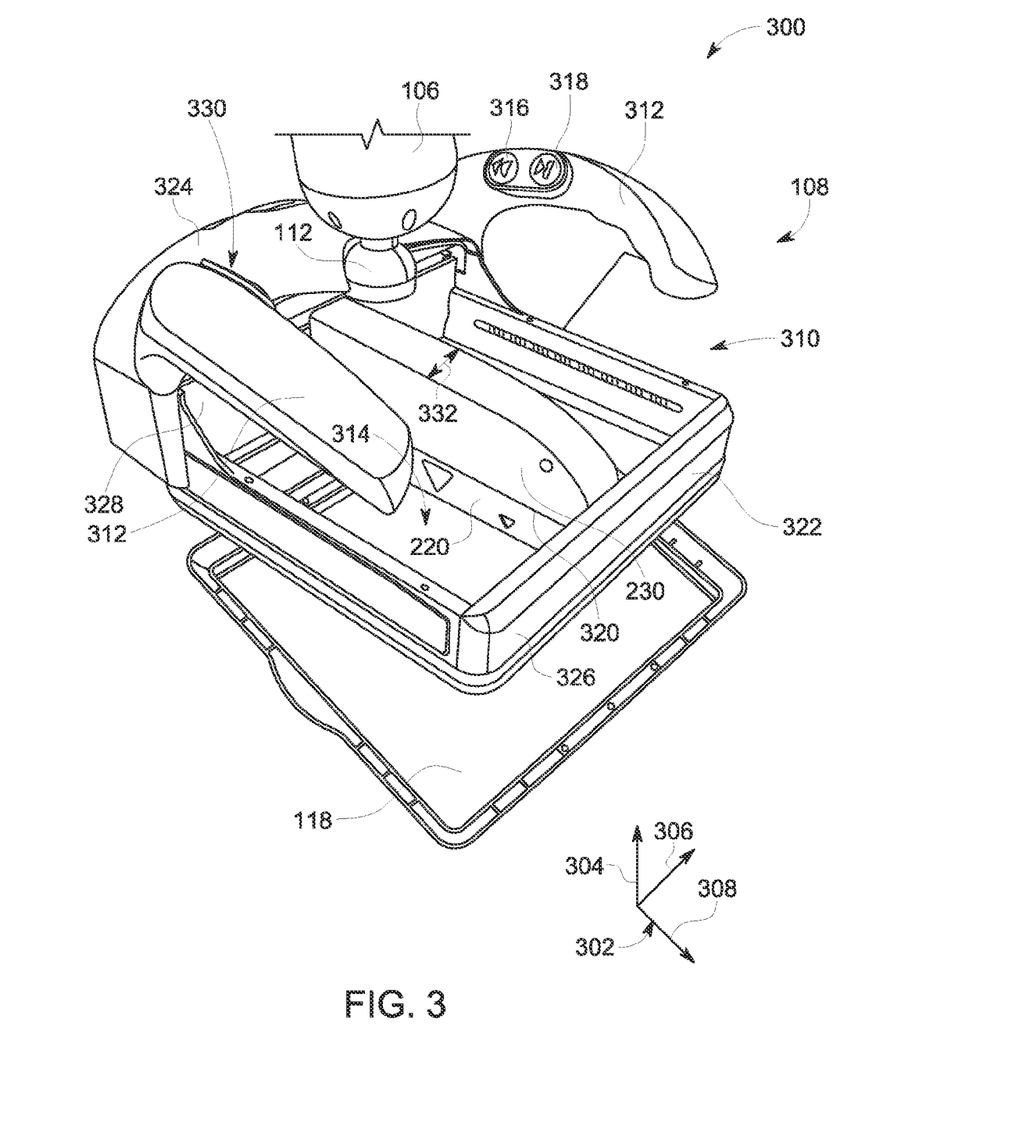
FIG. 3 shows a scanning assembly of a scanning apparatus according to an embodiment of the invention.

FIG. 3 shows a schematic 300 of an isometric view of the scanning assembly 108 coupled to the adjustable arm 106. The schematic 300 includes a coordinate system 302 including a vertical axis 304, horizontal axis 306, and a lateral axis 308.

The scanning assembly 108 includes a housing 310, the transducer module 220, and the module receiver 230. The housing 310 includes a frame 322 and a handle portion 324, the handle portion including two handles 312. The two handles 312 are opposite one another across a lateral axis of the scanning assembly 108, the lateral axis centered at the adjustable arm 106 and defined with respect to the lateral axis 308. The frame 322 is rectangular-shaped with an interior perimeter of the frame 322 defining an opening 314. The opening 314 provides a space (e.g., void volume) for translating the module receiver 230 and the transducer module 220 during a scanning procedure. In another example, the frame 322 may be another shape, such as square with a square-shaping opening 314. Additionally, the frame 322 has a thickness defined between the interior perimeter and an exterior perimeter of the frame 322.

The frame 322 includes four sets of side walls (e.g., the set including an interior side wall and an exterior side wall, the interior side walls defining the opening 314). Specifically, the frame 322 includes a front side wall 326 and a back side wall 328, the back side wall 328 directly coupled to the handle portion 324 of the housing 310 and the front side wall 326 opposite the back side wall 328 with respect to the horizontal axis 306. The frame 322 further includes a right side wall and a left side wall, the respective side walls opposite from one another and both in a plane defined by the vertical axis 304 and the lateral axis 308.

The frame 322 of the housing 310 further includes a top side and a bottom side, the top side and bottom side defined relative to the vertical axis 304. The top side faces the adjustable arm 106. A membrane 118 is disposed across the opening 314. More specifically, the membrane 118 is coupled to the bottom side of the frame 322. In one example, the membrane 118 is a membranous sheet maintained taut across the opening 314. The membrane 118 may be a flexible but non-stretchable material that is thin, water-resistant, durable, highly acoustically transparent, chemically resistant, and/or biocompatible. As discussed above, the bottom surface of the membrane 118 may contact a tissue (e.g., such as a breast) during scanning and a top surface of the membrane 118 may at least partially contact the transducer module 220 during scanning. As shown in FIG. 3, the membrane 118 includes a hard-shell clamping portion around a perimeter of the membrane. The clamping portion couples to the bottom side of the frame 322. In one example, the clamping portion may snap to a lip on the bottom side of the frame 322 of the housing 310 such that membrane 118 does not become uncoupled during scanning but is still removably coupled to the frame 322.

The handle portion 324 of the housing 310 includes two handles 312 for moving the scanning assembly 108 in space and positioning the scanning assembly 108 on a tissue (e.g., on a patient). In alternate embodiments, the housing 310 may not include handles 312. In one example, the handles 312 may be formed as one piece with the frame 322 of the housing 310. In another example, the handles 312 and the frame 322 may be formed separately and then mechanically coupled together to form the entire housing 310 of the scanning assembly 108.

As shown in FIG. 3, the scanning assembly 108 is coupled to the adjustable arm 106 through a ball joint 112 (e.g., ball-and-socket connector). Specifically, a top, domed portion of the handle portion 324 is coupled to the ball joint 112. The top portion of the handle portion 324 includes a concave depression forming a socket which a ball of the ball joint 112 fits into. The ball joint 112 is moveable in multiple directions. For example, the ball joint 112 provides rotational movement of the scanning assembly relative to the adjustable arm 106. The ball joint 112 includes a locking mechanism for locking the ball joint 112 in place and thereby maintaining the scanning assembly 108 stationary relative to the adjustable arm 106.

Additionally, as shown in FIG. 3, the handles 312 of the handle portion 324 include buttons for controlling scanning and adjusting the scanning assembly 108. Specifically, a first handle of the handles 312 includes a first weight adjustment button 316 and a second weight adjustment button 318. The first weight adjustment button 316 may decrease a load applied to the scanning assembly 108 from the adjustable arm 106. The second weight adjustment button 318 may increase the load applied to the scanning assembly 108 from the adjustable arm 106. Increasing the load applied to the scanning assembly 108 may increase an amount of pressure and compression applied to the tissue on which the scanning assembly 108 is placed. Further, increasing the load applied to the scanning assembly increases the effective weight of the scanning assembly on the tissue to be scanned. In one example, increasing the load may compress the tissue, such as a breast, of a patient. In this way, varying amounts of pressure (e.g., load) may be applied consistently with the scanning assembly 108 during scanning in order to obtain a quality image with the transducer module 220.

Before a scanning procedure, a user (e.g., ultrasound technician or physician) may position the scanning assembly 108 on a patient or tissue. Once the scanning assembly 108 is positioned correctly, the user may adjust the weight of the scanning assembly 108 on the patient (e.g., adjust the amount of compression) using the first weight adjustment button 316 and/or the second weight adjustment button 318. A user may then initiate a scanning procedure with additional controls on the handle portion 324 of the housing 310. For example, as shown in FIG. 3, a second handle of the handles 312 includes two additional buttons 330 (not individually shown). The two additional buttons 330 may include a first button to initiate scanning (e.g., once the scanning assembly has been placed on the tissue/patient and the amount of compression has been selected) and a second button to stop scanning. In one example, upon selecting the first button, the ball joint 112 may lock, thereby stopping lateral and horizontal movement of the scanning assembly 108.

The module receiver 230 is positioned within the housing 310. Specifically, the module receiver 230 is mechanically coupled to a first end of the housing 310 at the back side wall 328 of the frame 322, the first end closer to the adjustable arm 106 than a second end of the housing 310. The second end of the housing 310 is at the front side wall 326 of the frame 322. In one example, the module receiver 230 is coupled to the first end via a protrusion of the module receiver 230, the protrusion coupled to a motor (e.g., motor 232 described with reference to FIG. 2 above) of the module receiver 230.

As described above, the housing 310 is configured to remain stationary during scanning. In other words, upon adjusting a weight applied to the scanning assembly 108 through the adjustable arm 106 and then locking the ball joint 112, the housing 310 may remain in a stationary position without translating in the horizontal or lateral directions. However, the housing 310 may still translate vertically with vertical movement of the adjustable arm 106.

Conversely, the module receiver 230 is configured to translate with respect to the housing 310 during scanning. As shown in FIG. 3, the module receiver 230 translates horizontally, along the horizontal axis 306, with respect to the housing 310. The motor of the module receiver 230 may slide the module receiver 230 along a top surface of the first end of the housing 310.

The transducer module 220 is removably coupled with the module receiver 230. As a result, during scanning, the transducer module 220 translates horizontally with the module receiver 230. During scanning transducer module 220 sweeps horizontally across the breast under motor control of the module receiver 230 while a contact surface of the transducer module 220 is in contact with the membrane 118. The transducer module 220 and the module receiver 230 are coupled together at a module interface 320. The module receiver 230 has a width 332 which is the same as a width of the transducer module 220. In alternate embodiments, the width 332 of the module receiver may not be the same as the width of the transducer module 220. In some embodiments, the module interface 320 includes a connection 234 between the transducer module 220 and the module receiver 230, the connection 234 including a mechanical and electrical connection.

Figure 4:
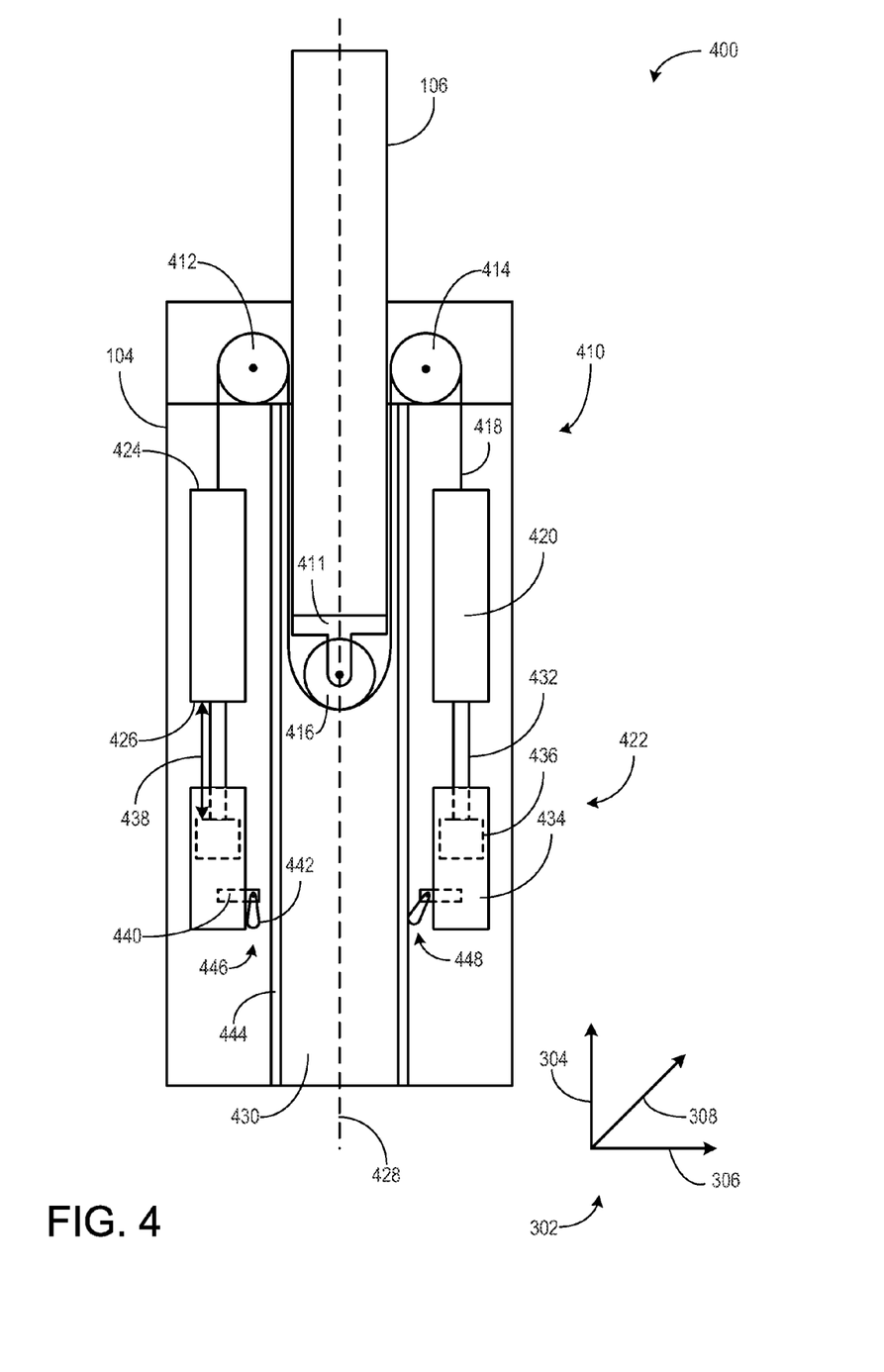
FIG. 4 shows a frame coupled to an adjustable arm of a scanning apparatus according to an embodiment of the invention.
Figure 5:
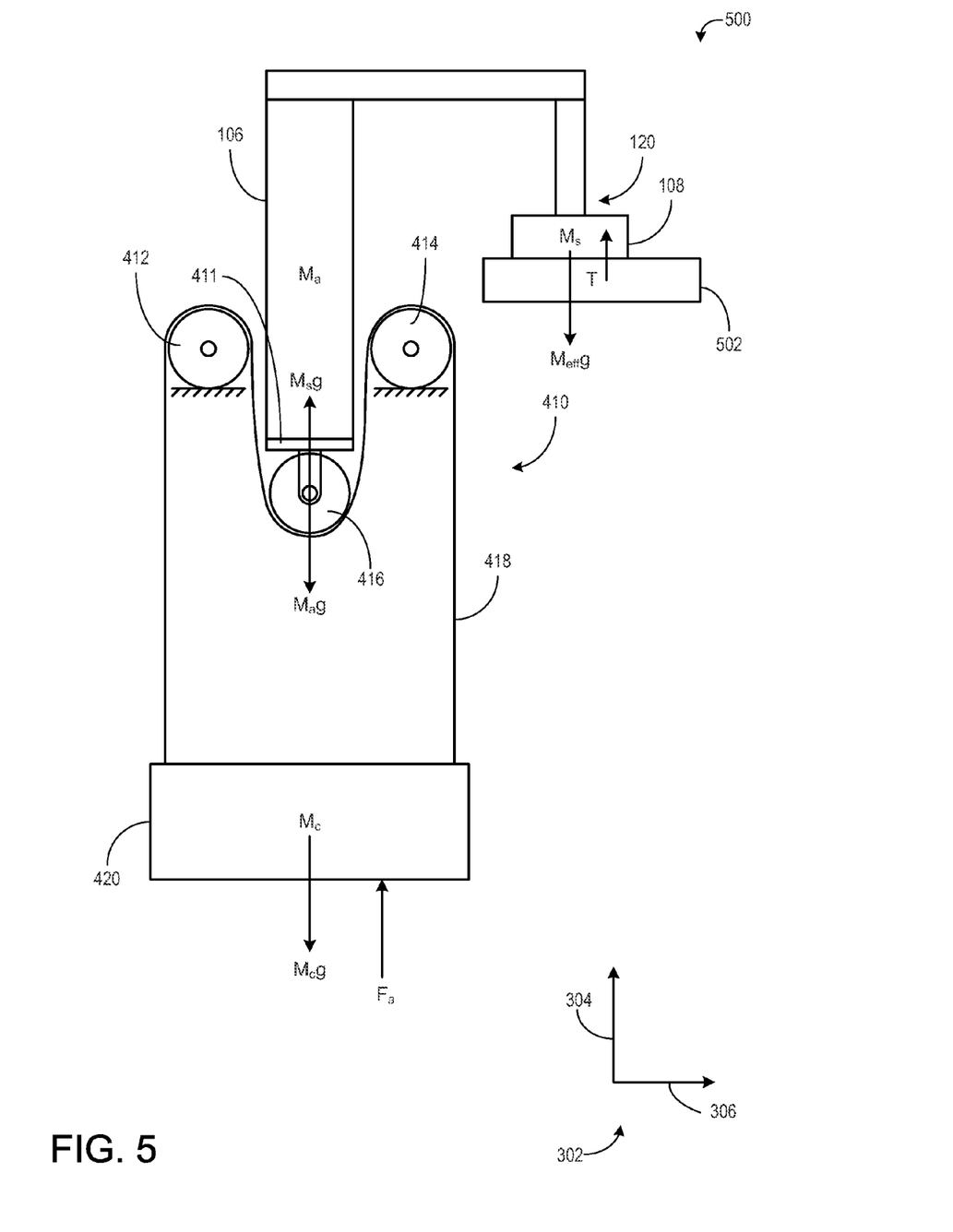
FIG. 5 shows forces acting on components of a scanning apparatus according to an embodiment of the invention.

FIGS. 4-5 show details of the adjustable arm 106 and frame 104 of the scanning apparatus 102 described above with reference to FIGS. 1-3. Specifically, FIG. 4 shows a schematic 400 of internal components of the frame 104 coupled to the adjustable arm 106. The schematic 400 includes the coordinate system 302 including the vertical axis 304, horizontal axis 306, and the lateral axis 308. FIG. 5 shows a schematic 500 of the forces acting on the components of the scanning apparatus 102.

The frame 104 includes a support system 410 which balances a weight of the adjustable arm 106 and scanning assembly 108 (shown in FIG. 1 and FIG. 5) and houses at least a portion of the adjustable arm 106 within the frame 104. The support system 410 includes a counterbalance system which counterbalances a weight of the scanning assembly to achieve an effective weight of the scanning assembly 108 on a tissue to be scanned (e.g., patient). The counterbalance system utilizes a system of pulleys and weights to adjust the counterbalancing and effective weight of the scanning assembly 108. As shown in FIG. 4, the support system 410 includes a first stationary pulley 412, a second stationary pulley 414, a third movable pulley 416, a cable 418, a counterweight 420, and a weight adjustment system 422.

As shown in FIG. 1 and FIG. 3, the first end 120 of the adjustable arm 106 is directly coupled to the scanning assembly through the ball joint 112. As shown in FIG. 4, a second end 411 of the adjustable arm 106 is positioned within the frame 104 and coupled directly to the third pulley 416. The third pulley 416 is movable (e.g., translatable) in an upward and downward direction relative to the stationary frame 104 and with respect to the vertical axis 304. However, the third pulley 416 may not be movable in horizontal and/or lateral directions with respect to the horizontal axis 306 and the lateral axis 308, respectively. As one example, the third pulley 416 may be coupled to the frame 104 at a center of the third pulley 416, along a lateral axis of the third pulley 416.

The third pulley 416 is positioned on the cable 418. Specifically, the third pulley 416 is positioned on a central portion of the cable 418. The cable 418 passes through two additional pulleys: the first pulley 412 and the second pulley 414. The first pulley 412 and the second pulley 414 are both stationary pulleys fixed to the frame 104. As such, the first pulley 412 and the second pulley 414 may rotate but not translate in any other direction (e.g., may not translate in the direction of the vertical axis 304, horizontal axis 306, or lateral axis 308). The first pulley 412 and the second pulley 414 are coupled to the frame 104 at the same horizontal position (with respect to the horizontal axis 306) but are opposite one another with respect to a central axis 428 of the frame 104. The third pulley 416 is a central pulley positioned along the central axis 428. As such, the third pulley 416 may move vertically along the central axis 428.

The frame 104 is cylindrical and centered along the central axis 428. Additionally, the frame 104 is at least partially hollow with one or more cavities formed therein. The adjustable arm 106 is centered within the frame 104 along the central axis 428. The adjustable arm 106 is movable vertically (with respect to the vertical axis 304) within a centralized cylindrical cavity 430 of the frame 104. A diameter of the adjustable arm 106 is slightly smaller than a diameter of the cavity 430 to allow sliding movement within the cavity 430.

The counterweight 420 is a cylinder with a hole running through the center of the counterweight 420 and along a length of the counterweight 420. As such, the counterweight 420 has a ring-shaped cross-section with an inner diameter and an outer diameter. Further, the counterweight 420 is centered along the central axis 428. The inner diameter of the counterweight 420 is larger than the diameter of the adjustable arm 106 and the outer diameter of the counterweight 420 is smaller than an outer diameter of the frame 104. In this way, the counterweight 420 fits within the frame 104 and around the cavity 430. Further, the counterweight 420 is not directly coupled to the frame 104 in order to allow free vertical movement of the counterweight 420 within the frame 104. In one example, the counterweight 420 translates vertically within a second cavity of the frame 104, the second cavity closer to an exterior housing of the frame 104 than the cavity 430.

A first end of the cable 418 is coupled to a first side of a first end 424 of the counterweight 420 and a second end of the cable 418 is coupled to a second side of the first end 424 of the counterweight 420. Further, the cable 418 extends at length between the two coupling points at the first end and the second end of the cable 418. The first side and the second side of the counterweight 420 are opposite one another with respect to the central axis 428. More specifically, the cable 418 is coupled to a top surface of the counterweight 420. The top surface at the first end 424 is proximate to the first pulley 412 and the second pulley 414 while a bottom surface of the counterweight 420 at the second end 426 is proximate to the weight adjustment system 422.

The cable 418 extends from the first side of the first end 424, through (e.g., over) the first pulley 412, through (e.g., under) the third pulley 416, through (e.g., over) the second pulley 414, and to the second side of the first end 424. As discussed above, the adjustable arm 106 is coupled to the third pulley 416 which sits on a loop (e.g., hammock) formed by the cable 418. The third pulley 416 is able to move in the vertical direction; however, it may not experience a large amount of movement since it may primarily balance forces between the first pulley 412 and the second pulley 414, as also shown in FIG. 5, discussed further below. In this way, the counterweight 420 is indirectly coupled to the adjustable arm 106 via the cable 418, the cable 418 coupled to two points on the top surface of the counterweight 420 (at the first end 424) and passing through two stationary pulleys (first pulley 412 and second pulley 414).

The weight adjustment system 422 includes a cylindrical body 434 having a ring-shaped cross-section with an inner diameter and an outer diameter. As shown in FIG. 4, the outer diameter of the body 434 of the weight adjustment system 422 is substantially equal to the outer diameter of the counterweight 420. However, in alternate embodiments, the outer diameter of the body 434 may be smaller or larger than the outer diameter of the counterweight 420. Despite the relative diameters, the outer diameter of the body 434 is smaller than the outer diameter of the frame 104 and the inner diameter of the body 434 is larger than the diameter of the cavity 430 and the diameter of the adjustable arm 106.

The weight adjustment system 422 further includes a first actuator 436 coupled to an adjustment bar 432. In one example, the first actuator 436 comprises a stepper motor. The first actuator 436 adjusts a vertical position of the adjustment bar 432 relative to a position of the weight adjustment system 422. The first actuator 436 of the weight adjustment system 422 is coupled to the counterweight 420 through the adjustment bar 432.

In one example, the weight adjustment system 422 may include one or more adjustment bars 434. A first end of each of the one or more adjustment bars 432 of the weight adjustment system 422 is coupled to a bottom surface of the second end 426 of the counterweight 420. A second end of each of the one more adjustment bars 432 is then coupled to the first actuator 436. In this way, the first actuator 436 may concurrently adjust a position of each of the one or more adjustment bars 432. In another example, the first actuator 436 may only be coupled to one of the one or more adjustment bars 432. The other adjustment bars 432 may then be mechanically coupled to the one adjustment bar 432 such that all of the adjustments bars 432 move together.

In one example, the weight adjustment system 422 may include three adjustment bars spaced equally around a circumference of the counterweight and/or the body 434 of the weight adjustment system 422. In another example, the weight adjustment system 422 may include more or less than three adjustment bars spaced equally around the circumference of the weight adjustment system 422 and/or counterweight 420 in order to balance and equally distribute the weight of the counterweight 420 on the weight adjustment system 422.

The first actuator 436 is movable into a finite number of positions. More specifically, the first actuator 436 adjusts a position of the adjustment bar 432 into the finite number of positions. The position of the adjustment bar 432 defines a vertical position (with respect to the vertical axis 304) of the counterweight 420 relative to the weight adjustment system 422. For example, the first actuator 436 increases a length 438 of the adjustment bar 432 to increase the vertical position of the adjustment bar 432 relative to the weight adjustment system 422. As the length 438 and vertical position of the adjustment bar 432 increases, a force applied to the counterweight 420 from the weight adjustment system 422 increases. As a result, the counterbalance to the scanning assembly provided by the counterweight may decrease and an effective weight of the scanning assembly 108 may increase. Adjusting the effecting weight of the scanning assembly 108 is discussed further below with reference to FIG. 5.

The weight adjustment system 422 further includes a second actuator 440 coupled to a locking mechanism 442. The locking mechanism 442 is configured to lock the weight adjustment system 422 to a guiding bar 444 of the frame 104. In one example, the guiding bar 444 includes two or more bars spaced equally around the frame 104 with respect to the central axis 428. In another example, the guiding bar 444 includes a hollow cylinder surrounding the adjustable arm 106. In this way, the guiding bar 444 may at least partially form the cavity 430.

As shown in FIG. 4, the locking mechanism 442 includes a self-locking clutch mechanism with one or more swinging pendulum-like clutches. At 446, the locking mechanism 442 is shown in an unlocked position wherein the clutch is proximate to the body 434 of the weight adjustment system 422 and not contacting the guiding bar 444. As a result, the weight adjustment system 422 may freely and vertically translate with the counterweight 420 within the frame 104. At 448, the locking mechanism 442 is shown in a locked position wherein the clutch is proximate to and contacting the guiding bar 444. The second actuator 440 may swing the clutch away from the weight adjustment system 422 and toward the guiding bar 444 in order to lock the weight adjustment system 422 in a specific vertical position. When the weight adjustment system 422 is in the locked position, it may not translate vertically within the frame 104. The second actuator 440 may activate the locking mechanism 442 from the unlocked position to the locked position in response to a signal received from a processor, such as from scanning processor 210 or in response to a user input, such as in response to a user depressing the second weight adjustment button 318. For example, the second actuator 440 may activate the locking mechanism 442 to lock the weight adjustment system 422 against the guiding bar 444 before adjusting the effective weight of the scanning assembly 108 on the tissue to be scanned. Further, if the locking mechanism 442 includes more than one clutches, the second actuator 440 may move all the clutches of the locking mechanism 442 together.

In an alternate embodiment, the locking mechanism 442 may include a pin locking system wherein the guiding bar includes a series of holes along a length of the guiding bar 444. The locking mechanism 442 may then include one or more pins positioned around the interior diameter of the body 434. To lock the weight adjustment system 422 to the guiding bar 444 of the frame 104, the second actuator may actuate the one or more pins to extend outwardly from the body 434 and toward the guiding bar 444 until the pin engages with a respective hole on the guiding bar 444.

In this way, when the weight adjustment system 422 is not locked to the frame 104, the weight adjustment system 422 moves vertically in tandem with vertical movement of the counterweight 420. However, upon locking the weight adjustment system 422 to the guiding bar 444, the weight adjustment system no longer moves vertically within the frame 104. Additionally, since the counterweight 420 is directly coupled to the weight adjustment system 422 through the adjustment bar 432, the counterweight 420 only moves vertically as the position of the adjustment bar 432 is adjusted.

Turning now to FIG. 5, schematic 500 shows masses of the components of the scanning apparatus 102 and the resulting forces on the system. More specifically, schematic 500 shows the scanning assembly 108 positioned on a tissue 502 to be scanned. In one example, the tissue is a breast of a patient. The scanning assembly 108 has a mass, $M_s$. The adjustable arm 106 is coupled to the scanning assembly 108 at the first end 120 of the adjustable arm 106. The adjustable arm 106 also has a mass, $M_a$.

As introduced above with regard to FIG. 4, the support system 410 includes a counterbalance system which counterbalances a weight of the scanning assembly 108 (e.g., weight equals $M_s g$) to achieve an effective weight, $M_{eff} g$ of the scanning assembly 108 on the tissue 502. The counterbalance system utilizes a system of pulleys and weights to adjust the counterbalancing and effective weight of the scanning assembly 108. FIG. 5 illustrates the components of the support system 410 and the forces acting upon those components.

The first pulley 412 and the second pulley 414 are shown in FIG. 5 as stationary pulleys (e.g., no translational movement) supporting the cable 418. The third pulley 416 is movable and sits within a loop formed by the cable 418. The second end 411 of the adjustable arm 106 is directly coupled to the third pulley 416. As a result the forces acting at the third pulley 416 include a negative, downward force $M_a g$ which is the weight of the adjustable arm 106 (wherein g is gravitational acceleration) and a positive, upward force $M_s g$ which is the weight of the scanning assembly 108.

The cable 418 is further coupled to the counterweight 420 at the two ends of the cable 418. The counterweight 420 has a mass, $M_c$, and the resulting force acting on the counterweight 420 is a negative, downward force of $M_c g$. In one example, the mass of the counterweight 420 $M_c$ may also include the mass of the weight adjustment system 422. A force from the weight adjustment system 422 also acts upon the counterweight. For example, as the first actuator 436 increases the length 438 of the adjustment bar 432, the vertical position of the counterweight 420 relative to the weight adjustment system 422 increases. Additionally, a positive, upward force, $F_a$, is applied to the counterweight 420 from the weight adjustment system 422. As the first actuator 436 increases the length 438 of the adjustment bar 432, the force $F_a$ increases.

The tissue 502 is at least partially elastic (e.g., similar to a spring) and therefore results in some vertical movement of the scanning assembly 108 when placed upon the tissue 502. If no counterbalancing was applied with the support system 410, the tissue 502 may feel the full weight, $M_s g$, of the scanning assembly 108. However, the weight of the adjustable arm, $M_a g$, weight of the counterweight 420, $M_c g$, and the force $F_a$ from the weight adjustment system 422 may offset and adjust the effective weight, $M_{eff} g$, of the scanning assembly 108 on the tissue (e.g., the effective weight felt by the patient).

The effective weight $M_{eff} g$ of the scanning assembly 108 may be determined by summing all the forces acting on the system shown in schematic 500. Since the scanning apparatus system is a relatively static system (e.g., not moving substantially when the scanning assembly is positioned on the tissue 502), all the forces in the system may approximately equal zero. Summing the forces described above and shown in schematic 500 results in the following equation:

$$-M_c g + F_a - M_a g + M_s g - M_{eff} g = 0 \quad (1)$$

The force $F_a$ may be based on a change in the length 438 of the adjustment bar 432 relative to the base length. For example, when the adjustment bar 432 is at the base length, $F_a$ may be substantially zero. As the first actuator 436 increases the length 438 from the base length, $F_a$ increases. Thus, $F_a$ may be based on the increase in length 438 of the adjustment bar 432. For example, increasing the length 438 by 5 mm (e.g., pushing upward and towards the counterweight 420 by 5 mm with the first actuator 436) may correspond to lifting approximately 2.3 kg. As a result, the mass of the counterweight $M_c$ may decrease by 2.3 kg. The lifting mass of the force $F_a$ may be referred to herein as the lift mass, $m_L$. Thus, equation 1 may be re-written to combine all the forces acting on the counterweight 420 and rearranged to solve for the effective weight $M_{eff} g$ of the scanning assembly 108:

$$-(M_c - m_L) g - M_a g + M_s g = M_{eff} g \quad (2)$$

The mass of the adjustable arm 106 $M_a$ and the mass of the scanning assembly 108 $M_s$ may then be combined to give a total mass of the scanning assembly 108 and adjustable arm 106 system $M_{SA}$, thereby giving the following equation:

$$M_{SA} - (M_c - m_L) = M_{eff} \quad (3)$$

As one example, the total mass of the scanning assembly 108 and adjustable arm 106 $M_{SA}$ may be substantially equal to the mass of the counterweight. The mass of the counterweight 420 $M_c$ may include the mass of the weight adjustment system 422 since the weight adjustment system 422 and the counterweight 420 are directly coupled together. Thus, the balanced mass of the weight adjustment system 422 and the counterweight 420 may substantially equal the total mass of the scanning assembly and adjustable arm. As a result, the effective mass of the scanning assembly $M_{eff}$ may be substantially equal to the lift mass $m_L$. In another example, the weight of the counterweight 420 and the weight of the weight adjustment system 422 may substantially equal the weight of the scanning assembly 108.

Before beginning a scanning procedure, the scanning assembly 108 may be completely counterbalanced such that the effective weight on the tissue 502 is approximately zero. More specifically, during positioning the scanning assembly 108 on the tissue 502, the weight adjustment system 422 may be unlocked (e.g., uncoupled) from the frame 104 and coupled to the counterweight 420. As a result, the upward force $F_a$ applied to (e.g., exerted onto) the counterweight 420 from the weight adjustment system 422 is substantially zero.

After positioning the scanning assembly 108 on the tissue 502, a user input (e.g., a user input from buttons on the scanning assembly 108, as shown in FIG. 3) may result in the second actuator 440 locking the weight adjustment system 422 to the guiding bar 444 of the frame 104. This position wherein the weight adjustment system 422 is locked to the frame 104 but not applying any force $F_a$ to the counterweight may be referred to herein as the base position. In the base position, the cable 418 may be completely taut.

Once the scanning assembly 108 is positioned on the tissue 502, the tissue exerts an upward force on the scanning assembly 108. The user may then adjust the amount of compression (e.g., loading) of the scanning assembly onto the tissue 502. In other words, inputs from a user (via buttons 316 and 318 shown in FIG. 3) may adjust the vertical position of the counterweight 420 relative to the weight adjustment system 422 via the adjustment bar 432 and first actuator 436, thereby adjusting the effective weight $M_{eff} g$ of the scanning assembly 108. As discussed above, the weight adjustment system 422 may be configured to adjust the effective weight $M_{eff} g$ of the scanning assembly 108 into a finite number of load zones. In one example, the finite number of load zones includes three zones in addition to the base position. In this example, the first actuator 436 adjusts the adjustment bar 432 into three different positions, each of the three positions resulting in transferring a respective load to the scanning assembly. For example, the first actuator 436 may adjust the adjustment bar 432 from the base position wherein the adjustment bar 432 is at the base length and no upward force is being applied to the counterweight 420 from the weight adjustment system 422 and into three positions, each position having a longer length 438 than subsequent positions. However, in other embodiments, other numbers of positions and load zones may be possible.

Each subsequent load zone may increase the effective weight of the scanning assembly 108. For example, a first zone may increase the effective weight from substantially zero to a first amount, the first amount greater than zero. The second zone may then increase the effective weight to a second amount, the second amount higher than the first amount. Finally, the third zone may increase the effective weight to a third amount, the third amount higher than the second amount. As one example, the third amount may be approximately the combined weight of the scanning assembly and adjustable arm $M_{SA}g$ such that substantially the full weight of the scanning assembly 108 is applied to the tissue 502 (and no counterbalancing is occurring).

As one example, the balanced mass of the scanning assembly 108 and the adjustable arm 106 $M_{SA}$ may be approximately 9.5 kg. A combined mass of the counterweight 420 and the weight adjustment system 422 may then be approximately 9.5 kg. In the base position, the effective mass $M_{eff}$ of the scanning assembly 108 is zero kg. When the weight adjustment system 422 is adjusted into zone 1, the counterweight 420 is lifted by a first amount and the resulting force $F_a$ applied the counterweight 420 may correspond to lifting the counterweight 420 by approximately 3.2 kg. As a result, the effective mass $M_{eff}$ of the scanning assembly 108 increases to 3.2 kg. Similarly, when adjusting the weight adjustment system 422 into zone 2, the counterweight 420 is lifted by a larger second amount and the resulting force $F_a$ corresponds to lifting the counterweight 420 by approximately 6.4 kg. As a result, the effective mass $M_{eff}$ of the scanning assembly 108 increases to 6.4 kg. Finally, when adjusting the weight adjustment system 422 into zone 3, the counterweight 420 is lifted by an even larger third amount and the resulting force $F_a$ corresponds to lifting the counterweight 420 by approximately 9.5 kg. As a result, the effective mass $M_{eff}$ of the scanning assembly 108 increases to 9.5 kg. In alternate embodiments, other combinations of zones and effective masses may be possible.

After adjusting the effective weight of the scanning assembly 108, the ball joint 112 may be locked. Even though the effective weighting of the scanning assembly 108 is locked into the desired position, the scanning assembly 108 remains vertically movable. Since the scanning assembly 108 is coupled through the adjustable arm 106 to the third movable pulley 416, the scanning assembly may continue to translate vertically with vertical movement of the tissue 502. Further, the cable 418 provides an amount of spring-like action allowing the cable to stretch and contract with vertical movement of the scanning assembly 108 and the adjustable arm 106, even when a weight adjustment zone has been chosen and "locked in". For example, as a patient breathes, the scanning assembly 108 may translate along with the patient's respiration. In this way, the support system 410 does not act as a vice upon the patient. Instead, the support system 410 is configured via the system of movable and stationary pulleys connected with the spring-like cable 418 to allow continuous vertical movement of the scanning assembly 108 while still applying the chosen amount of compression (e.g., effective weighting) to the tissue 502 via the scanning assembly 108. In this way, the scanning assembly 108 remains vertically movable relative to the frame 104 during positioning of the scanning assembly 108, adjusting the effective weighting of the scanning assembly 108, and during scanning wherein the weight adjustment system is locked to the frame 104.

As one embodiment, a system for imaging a tissue comprises an adjustable arm, a scanning assembly attached to a first end of the adjustable arm, a counterweight coupled to a second end of the adjustable arm, and a weight adjustment system coupled to the counterweight and configured to modify an effective weight of the scanning assembly. In one example, a total weight of the counterweight and weight adjustment system is equal to a weight of the scanning assembly.

The weight adjustment system comprises a first actuator, the first actuator coupled to the counterweight through an adjustment bar. A position of the adjustment bar defines a vertical position of the counterweight relative to the weight adjustment system. Additionally, the position of the adjustment bar is configured to be adjustable in order to adjust the effective weight of the scanning assembly, the position of the adjustment bar adjustable via the first actuator. In one example, the first actuator comprises a stepper motor.

The system further comprises a frame housing the weight adjustment system. The weight adjustment system further comprises a locking mechanism to lock the weight adjustment system to the frame at a desired position, the locking mechanism activated with a second actuator.

The counterweight is coupled to the adjustable arm via a cable, the cable coupled to two points on the counterweight and passing through a first stationary pulley and a second stationary pulley each fixed to the frame, a force of the first stationary pulley and a force of the second stationary pulley balanced by a third, movable pulley, the adjustable arm coupled to the third pulley.

The scanning assembly comprises a housing configured to remain stationary during scanning, a module receiver that is configured to translate with respect to the housing during scanning, and a transducer module coupled to the module receiver and comprising a transducer array of transducer elements. The housing defines an opening and the scanning assembly further comprises a membranous sheet disposed across the opening, the transducer module positioned to contact the membranous sheet during scanning. Additionally, the scanning assembly is coupled to the adjustable arm via a ball joint.

As another embodiment, an ultrasound scanning system for imaging a tissue, comprises an adjustable arm and a scanning assembly attached to a first end of the adjustable arm via a ball joint, the scanning assembly comprising a housing, a module receiver that is translatable with respect to the housing during scanning, and a transducer module coupled to the module receiver and comprising a transducer array of transducer elements, wherein the ball joint comprises a locking mechanism for immobilizing the scanning assembly relative to the adjustable arm.

The system further comprises a vertically movable pulley coupled to a second end of the adjustable arm, a counterweight coupled to a cable, the cable coupled to the vertically movable pulley through two stationary pulleys, and a weight adjustment system coupled to the counterweight via an actuator. A position of the actuator defines a load transferred from the counterweight to the scanning assembly when the scanning assembly is engaged with the tissue, the scanning assembly remaining vertically movable throughout the load transfer and scanning.

The weight adjustment system is lockable to a guiding bar fixed to a frame of the ultrasound scanning system. Additionally, the actuator is movable into three different positions, each of the three different positions transferring a respective load to the scanning assembly.

Figure 6:
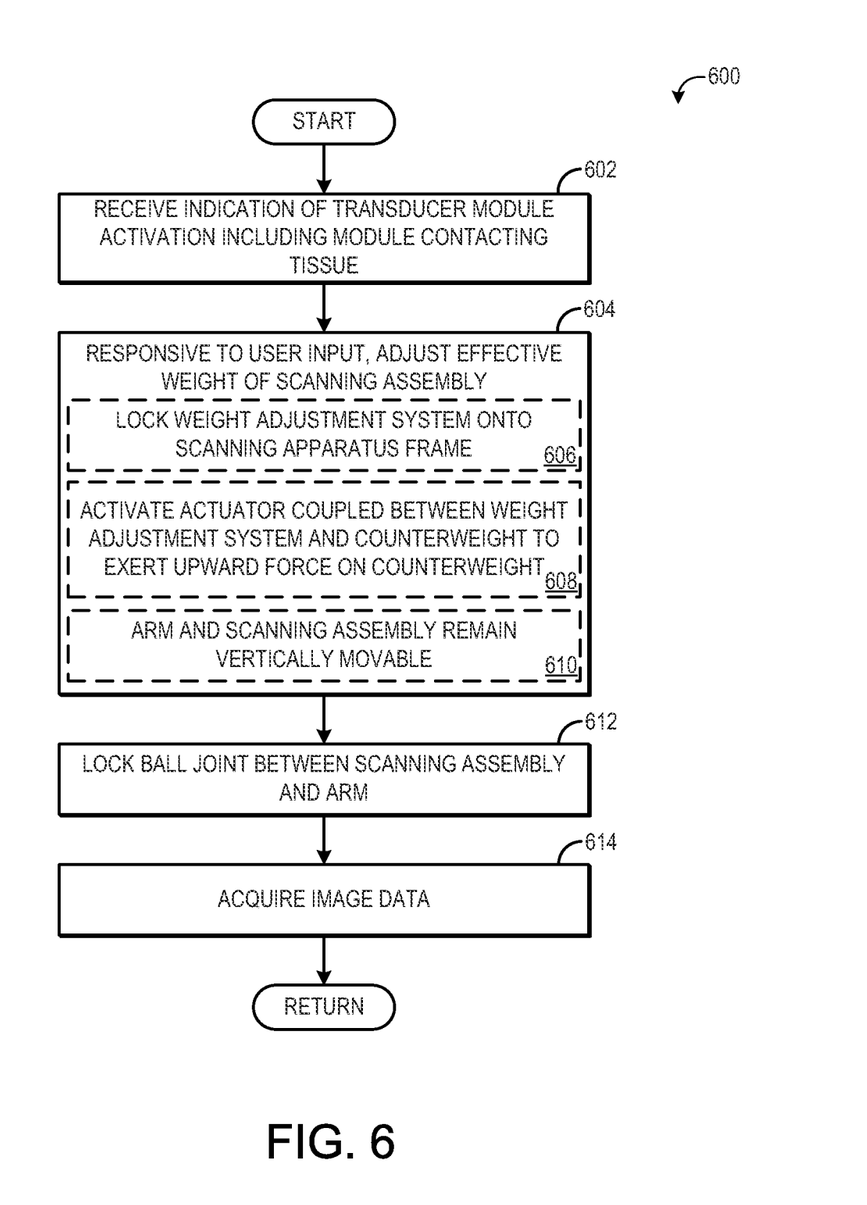
FIG. 6 shows a flow chart illustrating a method for adjusting a scanning assembly of a scanning apparatus configured to image a tissue according to an embodiment of the invention.

Turning now to FIG. 6, a method 600 for adjusting a scanning assembly of a scanning apparatus configured to image a tissue is illustrated. Method 600 may be performed by a processor, such as scanning processor 210, according to instructions stored thereon, in order to adjust the effective weight of a scanning assembly, such as the scanning assembly 108 of FIG. 1, prior to acquiring imaging data of a tissue.

The weight of the scanning assembly may be counterbalanced by a counterweight and weight adjustment system, as described above.

At 602, method 600 includes receiving an indication that the scanning assembly is contacting the tissue to be imaged. For example, an ultrasound technician, doctor, or other user may position the scanning assembly on a patient's tissue and subsequently enter an input to the scanning assembly instructing the scanning assembly to initiate scanning to acquire imaging data of the tissue. When the input is received, the module receiver (and attached transducer module) will be translated with respect to the scanning assembly housing to acquire ultrasound images of the tissue using ultrasound waves emitted by the transducer module. To acquire the images, the transducer module may be in contact with the tissue (via a membranous sheet in some examples). The indication that the scanning assembly is in contact with the tissue may include the user entering an input to initiate scanning or an input to adjust the effective weight of the scanning assembly (as explained below), or the indication may include an increase in pressure sensed by one or more pressure sensors of the transducer module.

During the positioning of the scanning assembly on the patient tissue, the scanning assembly may be substantially neutrally buoyant in space due to the counterweight and weight adjustment system providing a counterbalance for the weight of the scanning assembly. As such, the scanning assembly may be easily positioned on the tissue by the user. When the scanning assembly is initially positioned on and in contact with the tissue, little or no weight may be placed on the tissue by the scanning assembly.

In order to compress the tissue to increase the image quality of subsequently acquired images, the effective weight of the scanning assembly is adjusted, as indicated at 604. The adjustment of the effective weight of the scanning assembly may be performed in response to a user input, such as in response to a user depressing the second weight adjustment button 318 of FIG. 3 or other suitable input.

Adjusting the effective weight of the scanning assembly includes locking the weight adjustment system onto a frame of the scanning apparatus, as indicated at 606. As explained above, the weight adjustment system includes a weight adjustment block (e.g., a weight) coupled to the counterweight via an adjustment bar. The weight adjustment block is configured to translate vertically along with the counterweight during positioning of the scanning assembly. Once the scanning assembly is positioned at a desired location on the patient tissue (such that at least a portion of the scanning assembly is in contact with the patient), the weight adjustment block is fixed to the scanning apparatus frame in order to provide a platform against which the counterweight may be "pushed up," thus at least partially unbalancing the counterweight and scanning assembly to increase the effective weight of the scanning assembly on the tissue. The weight adjustment system includes an actuator that is activated to lock the weight adjustment system to the scanning apparatus frame.

Adjusting the effective weight of the scanning assembly also includes, at 608, activating an actuator coupled between the weight adjustment system and the counterweight to exert an upward force on the counterweight. The actuator of the weight adjustment system may comprise a stepper motor in one example that exerts an upward force on the counterweight by pushing up the adjustment bar coupling the weight adjustment block to the counterweight. The stepper motor may be adjustable to multiple, discrete positions such that the counterweight is lifted by either a first amount, a second amount, or a third amount. For example, when the counterweight and scanning assembly are balanced prior to adjusting the effective weight of the scanning assembly, substantially no weight is placed on the patient by the scanning assembly. If the stepper motor is activated to a first position, a first amount of upward force is exerted on the counterweight, resulting in a first effective weight of the scanning assembly (such as about 3 kg). A second position of the stepper motor may result in an effective weight of the scanning assembly of about 6.5 kg, and a third position of the stepper motor may result in an effective weight of the scanning assembly of about 9.5 kg. In some examples, the third position of the stepper motor may result in the cable coupled to the counterweight going slack. When the cable is slack, the counterweight is no longer providing any counterbalance to the scanning assembly, and the full weight of the scanning assembly is applied to the patient.

The effective weight of the scanning assembly applied to the patient may be selected by the user of the scanning apparatus to obtain an image of the tissue having a desired quality and may be based on characteristics of the tissue being imaged. For example, the user may be able to see the level of compression provided by the scanning assembly on the tissue by looking at the tissue through the transparent membrane. If the level of compression is not at a desired level, the user may adjust the effective weight of the scanning assembly to provide the desired compression. In a further example, the transducer of the scanning assembly may be activated during the adjustment of the effective weight of the scanning assembly so that the user can see a sample image of the tissue, via the display of the scanning apparatus for example. If the image is of a lesser quality than desired, the effective weight of the scanning assembly may be adjusted until the displayed image is of desired quality. The level of compression desired by the user to provide high-quality images may be based on the tissue being imaged. For example, if the tissue is dense, a different level of compression may be desired than if the tissue is less dense. In another example, the size the tissue may dictate the level of compression, such that larger breasts may utilize a higher level of compression than smaller breasts. In yet another example, the level of compression may be based on a comfort level of the patient being scanned. For example, a user may increase the level of compression until a patient becomes uncomfortable.

During the adjusting of the effective weight of the scanning assembly, the adjustable arm and scanning assembly remain vertically movable, as indicated at 610. As explained above with respect to FIGS. 4-5, the counterweight is coupled to the adjustable arm at one end of the adjustable arm (the adjustable arm being coupled to the scanning assembly at another end of the adjustable arm) via a cable and a movable pulley. The cable may act as a spring that provides a "zone of adjustment" (such as 5 cm) in which the load of the counterweight may be incrementally transferred to the scanning assembly. Within the zone of adjustment, the cable allows the vertically movable pulley, and thus the adjustable arm and scanning assembly, to translate vertically if the scanning assembly is pushed upwards by the patient (during patient respiration, for example). Once the counterweight has been lifted past the zone of adjustment, the cable goes slack and the adjustable arm will disengage with the counterweight and associated components.

Once the effective weight of the scanning assembly has been adjusted to a desired effective weight, method 600 proceeds to 612 to lock the ball joint between the scanning assembly and the adjustable arm. Locking the ball joint prevents additional adjustment of the pitch, yaw, rotation, etc., of the scanning assembly with respect to the adjustable arm during subsequent image acquisition. The ball joint may be locked in response to a user input, such as the user depressing a button to initiate scanning.

At 614, after the scanning assembly is positioned in the desired position on the patient, the desired effective weight of the scanning assembly has been applied to the patient, and the ball joint of the scanning assembly is locked, image data of the tissue is acquired by the scanning assembly. During the image acquisition, the scanning assembly and adjustable arm remain vertically movable while maintaining a relatively constant pressure (e.g., effective weight) with the scanning assembly. The image acquisition may include translating a transducer module and module receiver of the scanning assembly with respect to a stationary housing of the scanning assembly to horizontally sweep across the tissue. The transducer module may transmit and receive ultrasound waves and send the acquired raw image data (e.g., volumetric ultrasound echoes) to an image processor or other location for processing into a displayable image.

Thus, the method described above provides for positioning a counterbalanced scanning assembly onto a tissue of a patient prior to acquiring images of the tissue with the scanning assembly. Once the scanning assembly is in contact with the tissue at a desired location, the scanning assembly may be incrementally unbalanced from the counterbalance system via a weight adjustment system that exerts an upward force on a counterweight coupled to the scanning assembly. When the scanning assembly is unbalanced from the counterweight, the effective weight of the scanning assembly increases, providing increased compression of the tissue.

While the embodiments herein are described with respect to scanning assembly including modular transducer attached to a module receiver, other transducer configurations are possible. For example, the transducer may be fixed to the housing of the scanning assembly. Further, the weight adjustment system of the present disclosure may be used to counterbalance and adjust the effective weight of components other than an ultrasound imaging system, such as an x-ray imaging system, or a mechanical system such as a steam press.

In an embodiment, a method for adjusting a scanning assembly of a scanning apparatus configured to image a tissue comprises, while the scanning assembly is in contact with the tissue, adjusting an effective weight of the scanning assembly while the scanning assembly remains vertically movable, the scanning assembly coupled to an adjustable arm and counterbalanced by a counterweight and weight adjustment system via the adjustable arm; and while the scanning assembly further remains vertically movable, acquiring image data of the tissue with the scanning assembly.

Adjusting the effective weight of the scanning assembly may include adjusting the effective weight in response to a user input. Adjusting the effective weight of the scanning assembly may include transferring a load from the counterweight to the scanning assembly via an actuator of the weight adjustment system by exerting an upward force on the counterweight relative to the weight adjustment system, the actuator including a stepper motor. In one example, as the upward force increases, the effective weight of the scanning assembly on the tissue increases.

The method may further comprise locking the weight adjustment system to a frame of the scanning apparatus prior to adjusting the effective weight of the scanning assembly. The method further includes the adjustable arm remaining vertically moveable after locking the weight adjustment system to the frame, during the adjusting the effective weight of the scanning assembly, and during the acquiring of the image data. In en example, acquiring image data comprises acquiring volumetric ultrasound data. The method may further comprise locking a ball joint between the scanning assembly and the adjustable arm prior to acquiring the image data.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. An imaging system, comprising:
   an adjustable arm;
   an imaging assembly comprising a transducer, the imaging assembly attached to a first end of the adjustable arm;
   a counterweight coupled to a second end of the adjustable arm;
   a weight adjustment system including an adjustment bar and a first actuator coupled to the counterweight and configured to modify an effective weight of the imaging assembly;
   a frame housing the weight adjustment system; and
   a lock mechanism to look the weight adjustment system to the frame at a desired position;
   wherein the adjustment bar is coupled to a bottom of the counterweight and the first actuator is configured to adjust a length of the adjustment bar to adjust a position of the counterweight to modify the effective weight of the imaging assembly.

2. The system of claim 1, wherein a total weight of the counterweight and weight adjustment system is equal to a weight of the imaging assembly.

3. The system of claim 1, wherein the first actuator is coupled to the counterweight through the adjustment bar, and wherein the counterweight is indirectly coupled to the adjustable arm via a cable, the adjustment arm coupled to the cable via the counterweight.

4. The system of claim 3, wherein a position of the adjustment bar defines a vertical position of the counterweight relative to the weight adjustment system, and wherein the position of the adjustment bar is configured to be adjustable in order to adjust the effective weight of the imaging assembly, wherein the position of the adjustment bar is adjustable via the first actuator.

5. The system of claim 4, wherein the first actuator comprises a stepper motor.

6. The system of claim 4, wherein the lock mechanism is activated with a second actuator.

7. The system of claim 6, wherein the counterweight is coupled to the adjustable arm via a cable, the cable coupled to two points on the counterweight and passing through a first stationary pulley and a second stationary pulley each fixed to the frame, a force of the first stationary pulley and a force of the second stationary pulley balanced by a third, movable pulley, the adjustable arm coupled to the third pulley.

8. The system of claim 1, wherein the imaging assembly comprises a housing configured to remain stationary during imaging, a module receiver that is configured to translate with respect to the housing during imaging, and a transducer module coupled to the module receiver and comprising a transducer array of transducer elements.

9. The system of claim 8, wherein the housing defines an opening and further comprising a membranous sheet disposed across the opening, the transducer module positioned to contact the membranous sheet during imaging.

10. The system of claim 1, wherein the imaging assembly is coupled to the adjustable arm via a ball joint.

11. A method for adjusting a scanning assembly of a scanning apparatus configured to image a tissue, the scanning assembly coupled to an adjustable arm and counterbalanced by a counterweight and weight adjustment system via the adjustable arm, the method comprising:
    locking the weight adjustment system to a frame of the scanning apparatus;
    while the scanning assembly is in contact with the tissue, adjusting an effective weight of the scanning assembly while the scanning assembly remains vertically movable, the effective weight adjusted by adjusting a position of the counterweight via an adjustment bar and an actuator, the actuator and adjustment bar coupled to a bottom of the counterweight;
    locking a ball joint between the scanning assembly and the adjustable arm; and
    while the scanning assembly further remains vertically movable, acquiring image data of the tissue with the scanning assembly.

12. The method of claim 11, wherein the effective weight of the scanning assembly is adjusted in response to a user input.

13. The method of claim 11, wherein adjusting the effective weight of the scanning assembly includes transferring a load from the counterweight to the scanning assembly via the actuator of the weight adjustment system by exerting an upward force on the counterweight relative to the weight adjustment system, the actuator including a stepper motor, and wherein as the upward force increases, the effective weight of the scanning assembly on the tissue increases.

14. The method of claim 11, wherein the adjustable arm remains vertically moveable after locking the weight adjustment system to the frame, during the adjusting the effective weight of the scanning assembly, and during the acquiring of the image data.

15. The method of claim 11, wherein acquiring image data comprises acquiring volumetric ultrasound data.

16. An ultrasound scanning system for imaging a tissue, comprising:
    an adjustable arm;
    a scanning assembly configured for imaging the tissue, wherein the scanning assembly is attached to a first end of the adjustable arm via a ball joint, the scanning assembly comprising a housing, a module receiver that is translatable with respect to the housing during scanning, and a transducer module coupled to the module receiver and comprising a transducer array of transducer elements, wherein the ball joint comprises a lock mechanism for immobilizing the scanning assembly relative to the adjustable arm;
    a vertically movable pulley coupled to a second end of the adjustable arm; a counterweight coupled to a cable, the cable coupled to the vertically movable pulley through two stationary pulleys; and
    a weight adjustment system including an adjustment bar coupled to a bottom of the counterweight and an actuator coupled to the adjustment bar, wherein a position of the actuator defines a load transferred from the counterweight to the scanning assembly when the scanning assembly is adapted to be engaged with the tissue, the scanning assembly remaining vertically movable throughout the load transfer and imaging of the tissue.

17. The system of claim 16, wherein the weight adjustment system is lockable to a guiding bar fixed to a frame of the ultrasound scanning system.

18. The system of claim 16, wherein the actuator is movable into three different positions, each of the three different positions transferring a respective load to the scanning assembly.

* * * * *

UNITED STATES PATENT AND TRADEMARK OFFICE
CERTIFICATE OF CORRECTION

PATENT NO.         : 9,597,056 B2
APPLICATION NO.    : 14/042565
DATED              : March 21, 2017
INVENTOR(S)        : Summers et al.

Page 1 of 1

It is certified that error appears in the above-identified patent and that said Letters Patent is hereby corrected as shown below:

In the Claims

Column 20, Line 51, Claim 1, replace "look" with "lock".

Signed and Sealed this
Ninth Day of May, 2017

Michelle K. Lee
*Director of the United States Patent and Trademark Office*